US007971997B2

(12) United States Patent
Hiramatsu et al.

(10) Patent No.: US 7,971,997 B2
(45) Date of Patent: Jul. 5, 2011

(54) APPARATUS FOR SELECTING AN INTRAOCULAR LENS AND A METHOD OF SELECTING THE INTRAOCULAR LENS

(75) Inventors: Hiroyuki Hiramatsu, Toyokawa (JP); Yukinobu Ban, Nishio (JP)

(73) Assignee: Nidek Co., Ltd., Gamagori-shi (JP)

( * ) Notice: Subject to any disclaimer, the term of this patent is extended or adjusted under 35 U.S.C. 154(b) by 199 days.

(21) Appl. No.: 12/222,021

(22) Filed: Jul. 31, 2008

(65) Prior Publication Data

US 2009/0281552 A1 Nov. 12, 2009

(30) Foreign Application Priority Data

Aug. 3, 2007 (JP) .................................. 2007-203685

(51) Int. Cl.
*A61B 3/10* (2006.01)
(52) U.S. Cl. ........ 351/212; 351/246; 623/6.11; 606/107
(58) Field of Classification Search .................... 351/212
See application file for complete search history.

(56) References Cited

U.S. PATENT DOCUMENTS

| 5,907,388 | A | 5/1999 | Fujieda |
| 7,370,969 | B2 | 5/2008 | Klyce et al. |
| 2002/0103479 | A1* | 8/2002 | Sarver ............................... 606/4 |
| 2004/0156014 | A1* | 8/2004 | Piers et al. ..................... 351/168 |
| 2004/0249729 | A1* | 12/2004 | Matsumura et al. ............ 705/28 |
| 2005/0225721 | A1* | 10/2005 | Harris et al. ................... 351/200 |
| 2008/0004698 | A1* | 1/2008 | Das et al. ...................... 623/6.22 |

FOREIGN PATENT DOCUMENTS

| JP | A-10-108837 | 4/1998 |
| JP | A-2002-119470 | 4/2002 |
| JP | A-2005-288176 | 10/2005 |

* cited by examiner

*Primary Examiner* — Jessica T Stultz
(74) *Attorney, Agent, or Firm* — Oliff & Berridge, PLC

(57) ABSTRACT

An intraocular lens selection apparatus and an intraocular lens selection method for selecting an intraocular lens to be implanted into an examinee's eye. The apparatus has an input unit which inputs corneal wavefront aberration of the eye, a memory which stores wavefront aberrations of a plurality of intraocular lens models, an unit which sets, as a target value, desired post-operative residual wavefront aberration of the eye after the lens is implanted, an unit which calculates, as an estimated value, post-operative residual wavefront aberration of the eye to be obtained when each lens model is implanted, based on the inputted corneal wavefront aberration and the stored wavefront aberration of each lens model, and specifies one of the lens models which renders the estimated value close to the set target value, a monitor, and a display control unit which controls the monitor to display information of the specified lens model.

2 Claims, 8 Drawing Sheets

APPARATUS FOR SELECTING AN INTRAOCULAR LENS AND A METHOD OF SELECTING THE INTRAOCULAR LENS

BACKGROUND OF THE INVENTION

1. Field of the Invention

The present invention relates to an intraocular lens selection apparatus and an intraocular lens selection method for selecting an intraocular lens to be implanted into an examinee's eye.

2. Description of Related Art

Conventionally, there is known a method for prescribing an intraocular lens to be implanted into an examinee's eye which obtains corneal refractive power and an ocular axial length of the examinee's eye and determines a diopter of the intraocular lens using the obtained values and a predetermined calculation formula for the intraocular lens. Further, there is proposed an apparatus which determines (or selects) the diopter of the intraocular lens depending on desired post-operative refractive power of the examinee's eye (see Japanese Patent Application Unexamined Publication No. 2002-119470).

However, intraocular lenses from various manufacturers could have different wavefront aberrations (e.g., spherical aberrations) even if they have the same diopters, and no account has been taken for the difference between the wavefront aberrations when the intraocular lens is prescribed using the above-mentioned method or the above-mentioned apparatus.

SUMMARY OF THE INVENTION

An object of the invention is to provide an intraocular lens selection apparatus and an intraocular lens selection method each capable of selecting an intraocular lens suitable for an examinee's eye.

To achieve the object and in accordance with the purpose of the present invention, an intraocular lens selection apparatus for selecting an intraocular lens to be implanted into an examinee's eye comprises an input unit which inputs corneal wavefront aberration of the examinee's eye, a memory which stores wavefront aberrations of a plurality of intraocular lens models, a setting unit which sets, as a target value, desired post-operative residual wavefront aberration of the examinee's eye after the intraocular lens is implanted, a calculation unit which calculates, as an estimated value, post-operative residual wavefront aberration of the examinee's eye to be obtained when each intraocular lens model is implanted, based on the inputted corneal wavefront aberration and the stored wavefront aberration of each intraocular lens model, and specifies one of the intraocular lens models which renders the estimated value close to the set target value, a monitor, and a display control unit which controls the monitor to display information of the specified intraocular lens model.

In another aspect of the present invention, an intraocular lens selection method for selecting an intraocular lens to be implanted into an examinee's eye, the method comprises the steps of inputting corneal wavefront aberration of the examinee's eye, setting, as a target value, desired post-operative residual wavefront aberration of the examinee's eye after the intraocular lens is implanted, calculating, as an estimated value, post-operative residual wavefront aberration of the examinee's eye to be obtained when each intraocular lens model is implanted, based on the inputted corneal wavefront aberration and the wavefront aberration of each intraocular lens model, and specifying one of the intraocular lens models which renders the estimated value close to the set target value.

Additional objects and advantages of the invention are set forth in the description which follows, are obvious from the description, or may be learned by practicing the invention. The objects and advantages of the invention may be realized and attained by the intraocular lens selection apparatus and the intraocular lens selection method in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

FIG. 4 is a view showing a screening screen;

FIG. 7 is a view showing an intraocular lens selection screen, and

DETAILED DESCRIPTION OF THE PREFERRED EMBODIMENTS

Figure 1:
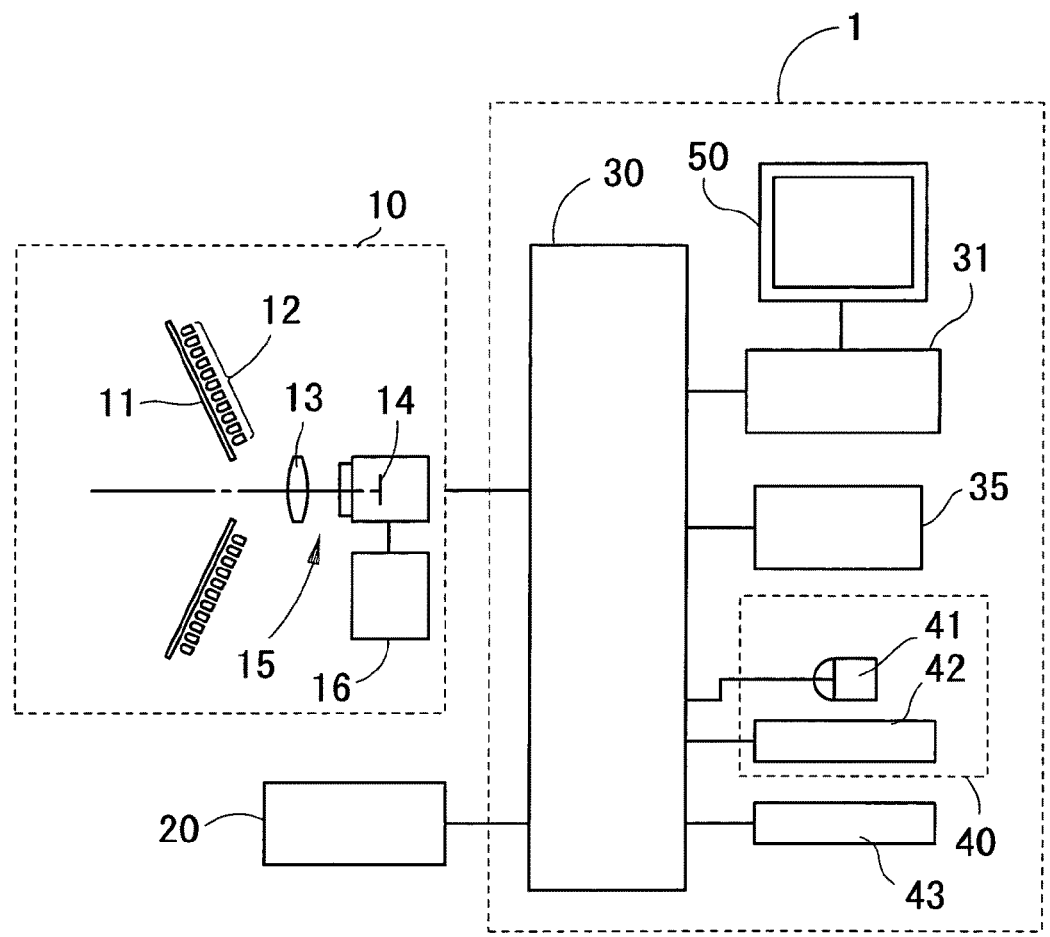
FIG. 1 is a schematic block diagram showing an intraocular lens selection apparatus according to a preferred embodiment of the present invention.

A detailed description of preferred embodiments of an intraocular lens selection apparatus and an intraocular lens selection method embodied by the present invention is provided below with reference to the accompanying drawings. FIG. 1 is a schematic block diagram of an intraocular lens selection apparatus according to a preferred embodiment of the present invention.

An intraocular lens selection apparatus 1 comprises a Central Processing Unit (hereinafter, referred to as "CPU") (i.e., a calculation control unit) 30, an Image Processing Unit (hereinafter, referred to as "IPU") (i.e., a display control unit) 31, a memory (i.e., a storage unit) 35, an input unit 40, a printer (i.e., a printing unit) 43, a monitor (i.e., a display unit) 50, and other constituent elements which are connected preferably via a bus.

The CPU 30 controls an operation of each unit in accordance with an intraocular lens selection program, a control program, and other programs, which have been stored in the memory 35. The IPU 31 controls a screen display on the monitor 50. The memory 35 is constructed by a hard disc drive and other constituent elements and preferably stores the various programs executed in the CPU 30, intraocular lens model information, surgeon information, measurer information, and calculation formulae for finding a diopter of the intraocular lens. In the preferred embodiment of the present invention, the input unit 40 comprises a mouse 41 and a keyboard 42 which has various keys. It is added that a commercially-available personal computer system may be used as the CPU 30, the IPU 31, the memory 35, the input unit 40 and the monitor 50, and the various programs and other items may be installed in the commercially-available personal computer system.

Further, to the apparatus 1, a corneal shape measurement apparatus 10 and an ocular axial length measurement apparatus 20 for obtaining measurement data of the examinee's eye for use in selecting the intraocular lens are connected. The apparatus 10 is adapted to measure corneal wavefront aberration by projecting measurement light onto a cornea of the examinee's eye and photo-receiving the light reflected therefrom. Examples of the apparatus 10 include an apparatus which measures a corneal shape by projecting a placido ring target onto the cornea and photo-receiving a reflection image of the placido ring target, and an apparatus which measures the corneal shape by using a principle of optical interference.

The apparatus 10 according to the preferred embodiment of the present invention comprises a placido plate 11 in which a plurality of placido rings are formed, a light source 12 substantially uniformly illuminating the placido plate 11 from behind, an image-pickup optical system 15 which comprises an image-pickup lens 13 and a two-dimensional image-pickup element 14 both for use in picking up a ring pattern image projected onto the cornea of the examinee's eye, and a control unit 16. Further, the apparatus 10 according to the preferred embodiment of the present invention comprises a measurement optical system which measures eye refractive power distribution or the wavefront aberration of the examinee's eye by projecting measurement light onto a fundus of the examinee's eye and photo-receives the light reflected therefrom (not shown) (see an optical system disclosed in U.S. Pat. No. 5,907,388 (corresponding to Japanese Patent Application Unexamined Publication No. Hei10-108837). Still further, the apparatuses 1 and 10 are connected to each other, and a set of data obtained by the apparatus 10 is transferred to and stored in the memory 35 of the apparatus 1.

Yet further, examples of the apparatus 20 include an apparatus which measures the ocular axial length by making an ultrasonic probe into contact with the examinee's eye and receiving a return echo therefrom, and an apparatus which measures the ocular axial length by using a principle of optical interference.

Additionally, the intraocular lens model information stored in the memory 35 is information pertaining to intraocular lens models supplied form various manufacturers, and preferably includes a manufacturer name, a model name, an A constant, a depth of an anterior chamber (mm), spherical aberration (μm). It is added that the spherical aberration of each intraocular lens model disclosed in the preferred embodiment of the present invention is indicative of the spherical aberration to be corrected when the intraocular lens is implanted into the examinee's eye.

The surgeon information stored in the memory 35 is information pertaining to a surgeon who operates the implantation of the intraocular lens, and preferably includes a name of the surgeon, information pertaining to each intraocular lens model which is to be used by the surgeon, post-operative residual spherical aberration of the examinee's eye desired by the surgeon.

The measurer information stored in the memory 35 is information pertaining to a measurer who performs ocular axial length measurement on the examinee's eye and preferably includes a name of the measurer, and a correction value (required where contact-type method is employed for the measurement).

Figure 2:
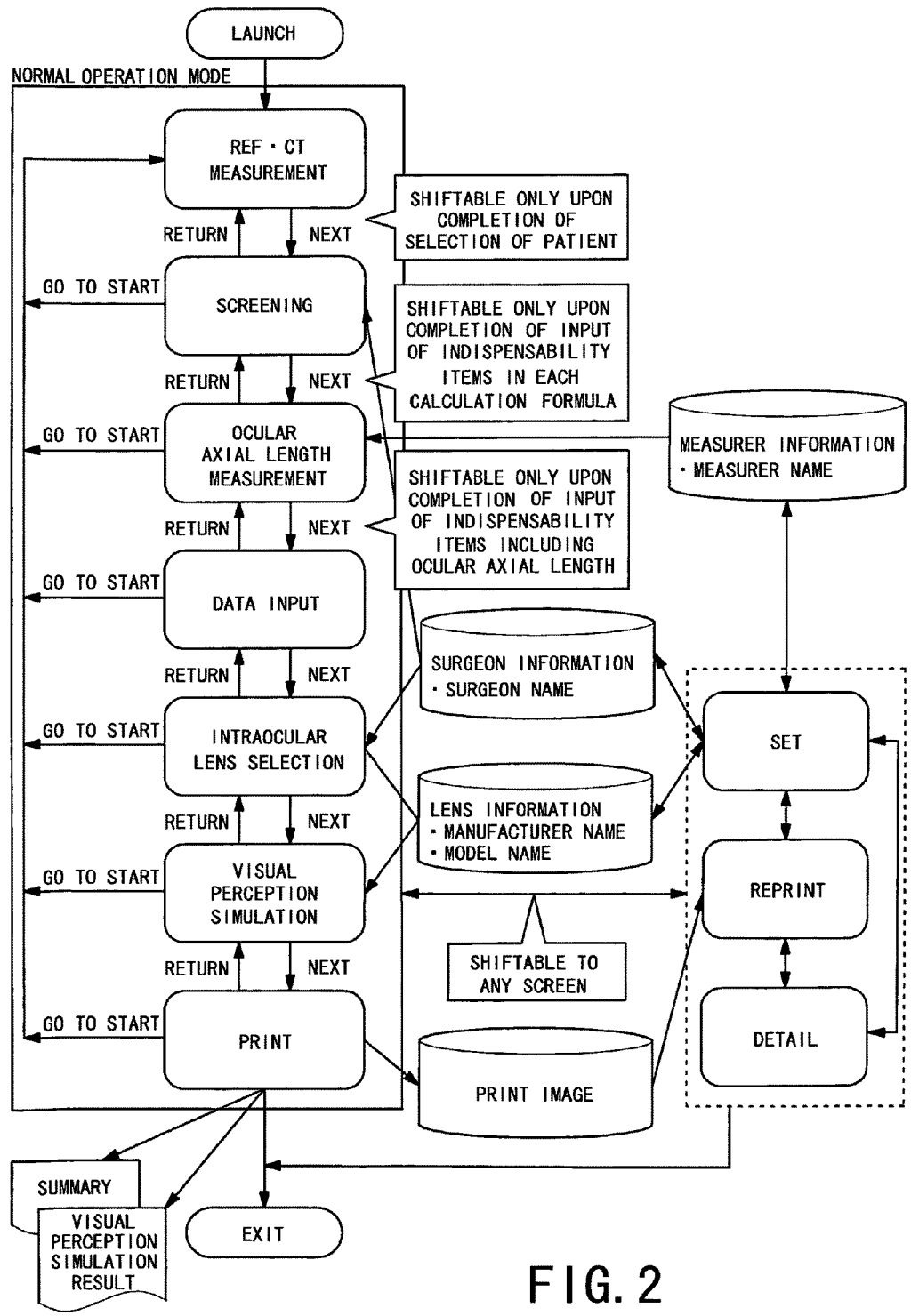
FIG. 2 is a flow chart showing operations of the intraocular lens selection apparatus.
Figure 3:
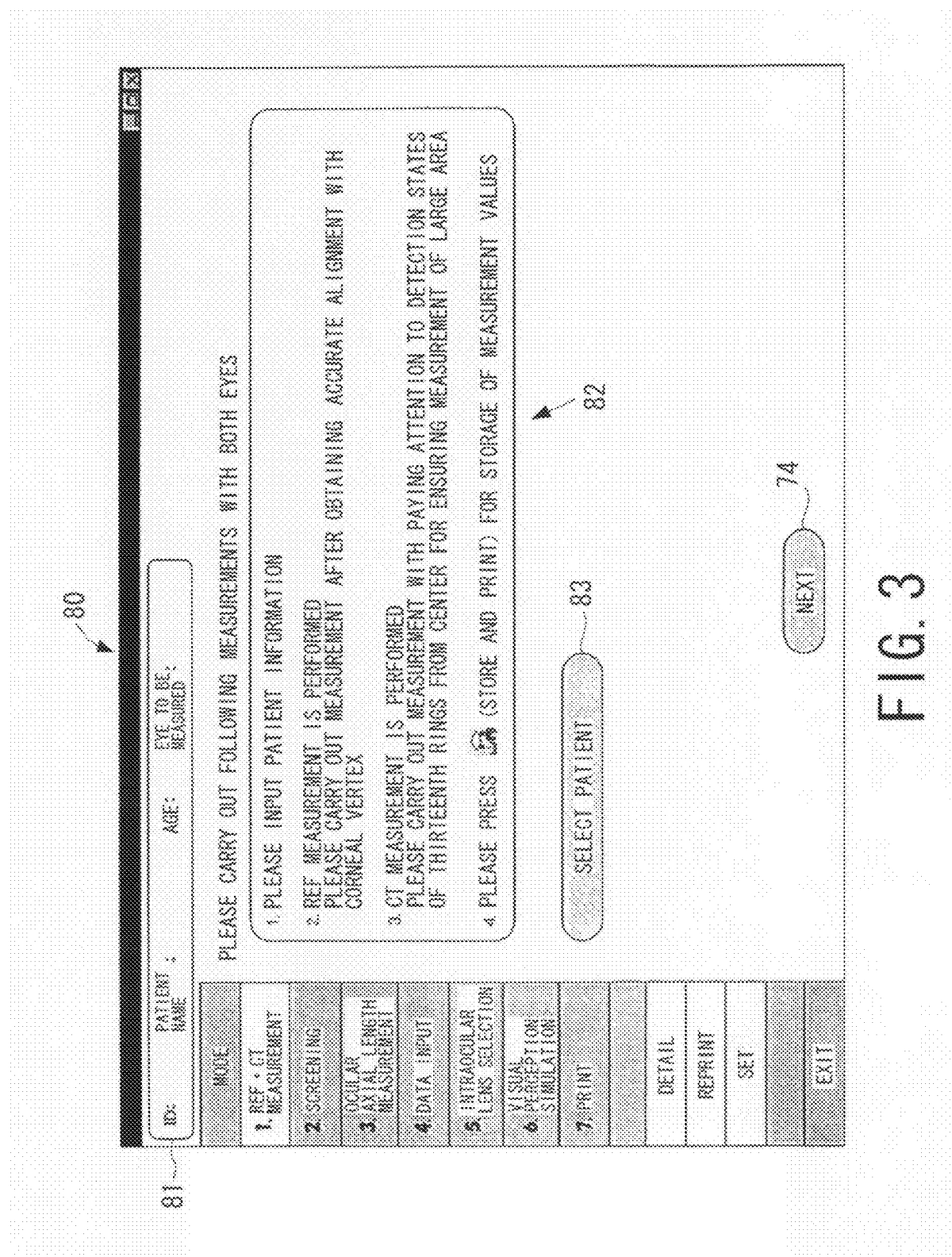
FIG. 3 is a view showing an REF•CT measurement screen.

FIG. 2 is a flow chart showing operations of the intraocular lens selection apparatus. The intraocular lens selection apparatus preferably has various modes including an REF•CT measurement mode, a screening mode, an ocular axial length measurement mode, a data input mode, an intraocular lens selection mode, a visual perception simulation mode, and a print mode.

Further, when changing an operation mode, a mode shift button 74 is used for entering (returning to) a next operation mode, and a mode shift button 75 is used for entering (returning to) a previous operation mode (see FIGS. 3-8).

Upon activation of a program, the CPU 30 enters an REF•CT measurement screen (or mode) 80. The screen 80 preferably comprises a display field 81 for displaying patient information, a display field 82 for displaying an explanation of a measuring procedure, and a patient selection button 83.

Clicking on the button 83 allows a previously-registered patient list to be displayed on the monitor 50. By selecting a patient who is concerned from the list, information pertaining to the selected patient (e.g., an ID number, a name, an age, and a sex) is obtained. It is added that the procedure may also be achieved by directly inputting the patient information with the input unit 40.

Next, the apparatus 10 measures the eye refractive power distribution or the wavefront aberration of the examinee's eye (i.e., REF measurement). Additionally, the apparatus 10 picks up an anterior segment image of the examinee's eye with the placido ring image (i.e., CT measurement). The control unit 16 of the apparatus 10 obtains information (i.e., measurement values) such as corneal height distribution which is a three-dimensional shape of a corneal surface, corneal curvature distribution, and corneal refractive power distribution based on the placido ring image in the picked up anterior segment image. Further, the apparatus 10 obtains the corneal wavefront aberration in a predetermined analytical diameter by way of a comparison between the obtained corneal height distribution and corneal height distribution with the aberration assumed to be zero. Still further, based on the picked up anterior segment image, the apparatus 10 detects a corneal vertex and a pupillary center of the examinee's eye and obtains an amount and a direction of deviation therebetween.

Upon completion of the calculation of the measurement values performed by the control unit 16 as mentioned above, the obtained measurement values are automatically transferred to and stored in the memory 35. It is added that the calculation of the measurement values may be performed by the CPU 30.

Figure 4:
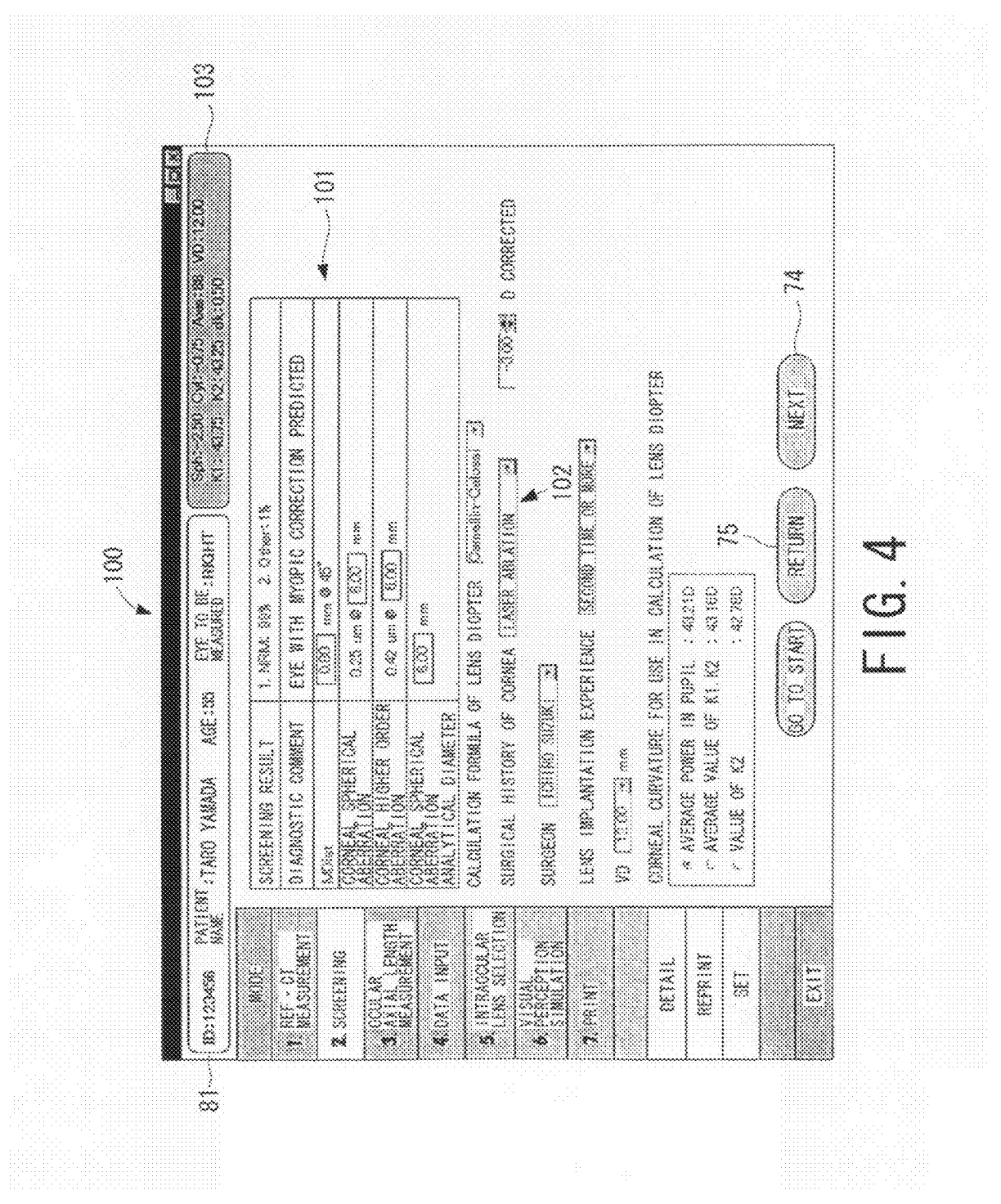

After the REF•CT measurement is completed and the button 74 is clicked on, then the CPU 30 enters a screening screen (or mode) 100 as shown in FIG. 4.

The screen 100 preferably comprises a display field 101 for displaying information based on the measurement values transferred from the apparatus 10, a display field 102 for displaying information to be inputted for the calculation of the diopter of the intraocular lens, a display field 103 for displaying a measurement result (e.g., the eye refractive power distribution, VD (Vertex Distance), and the corneal refractive power distribution) which have been obtained in the REF CT measurement mode.

The display field 101 preferably displays a result of screening, a diagnostic comment, MDist (Mahalanobis Distance), the corneal spherical aberration, corneal higher order aberration, and an analytical diameter of the corneal spherical aberration. The result of the screening is an analytical result obtained by the CPU 30 based on the presence/absence of corneal abnormalities in the examinee's eye, which predicts one of items including a normal eye (astigmatic power within 0.5D), an astigmatic eye (astigmatic power over 0.5D), keratoconus suspected, keratoconus, corneal degeneration, corneal transplantation performed, myopic correction performed, hyperopic correction performed, and others. The diagnostic comment is made based on the result of the screening. Additionally, FIG. 4 indicates that the examinee's eye is classified as "normal eye" with a probability of 99%, while the examinee's eye is classified as "others" with a probability of 1%. It is added that, a detail of the method for the corneal analysis is disclosed in U.S. Pat. No. 7,370,969 (corresponding to Japanese Patent Application Unexamined Publication No. 2005-288176).

The MDist is indicative of the amount and the direction of deviation between the corneal vertex and the pupillary center of the examinee's eye, and the amount of the deviation is expressed in mm, while the direction of the deviation is expressed in degrees (°). The CPU 30 determines whether the amount of the deviation is normal. For example, the amount of the deviation is determined to be "normal" when it is equal to or more than 0 mm and less than 0.3 mm, "abnormality suspected" when equal to or more than 0.3 mm and less than 0.5 mm, and "abnormal" when equal to or more than 0.5 mm.

The corneal spherical aberration is indicative of the spherical aberration which is one of higher order aberration components found in the cornea of the examinee's eye, and is expressed in μm (an analytical diameter of the corneal spherical aberration is additionally displayed).

The corneal higher order aberration is indicative of the sum of the higher order aberration components (the higher order aberration components each being defined as a component of the Zernike's polynomial which is equal to or greater than a third-order component), and is expressed in μm (an analytical diameter of the corneal higher order aberration is additionally displayed).

The analytical diameter of the corneal spherical aberration is indicative of the diameter of a corneal region of the examinee's eye which is obtained at the time when the control unit 16 of the apparatus 10 obtains the corneal wavefront aberration of the examinee's eye. The CPU 30 determines the size of the analytical diameter. For example, the analytical diameter is determined to be "normal" when it is equal to or more than 6 mm, "abnormality suspected" when equal to or more than 5 mm and less than 6 mm, and "abnormal" when less than 5 mm.

The display field 102 preferably displays the calculation formula for finding the diopter of the intraocular lens, a history of surgery on the cornea, a surgeon name, a presence/absence of an experience of the intraocular lens implantation, VD (Vertex Distance), and corneal curvature. The calculation formula for finding the diopter of the intraocular lens is selectable. It is added that the calculation formula for finding the diopter of the intraocular lens is preferably selected from Camellin-Calossi, SRK, SRK-2, SRK-T, BINKHORST, HOFFER-Q, and Holladay.

The history of the surgery on the cornea is selectable. In the preferred embodiment of the present invention, the history of the surgery on the cornea is selected from no surgery experienced, incision such as RK (Radial Keratotomy) experienced, laser ablation such as PRK (Photo Refractive Keratectomy) experienced, and the implantation experienced. Further, a correction value (expressed in diopter) may be inputted through an input operation. The input correction value is used for the calculation for finding the diopter of the intraocular lens. Still further, the corneal curvature is selectable which is used for the calculation for finding the diopter of the intraocular lens.

Figure 5:
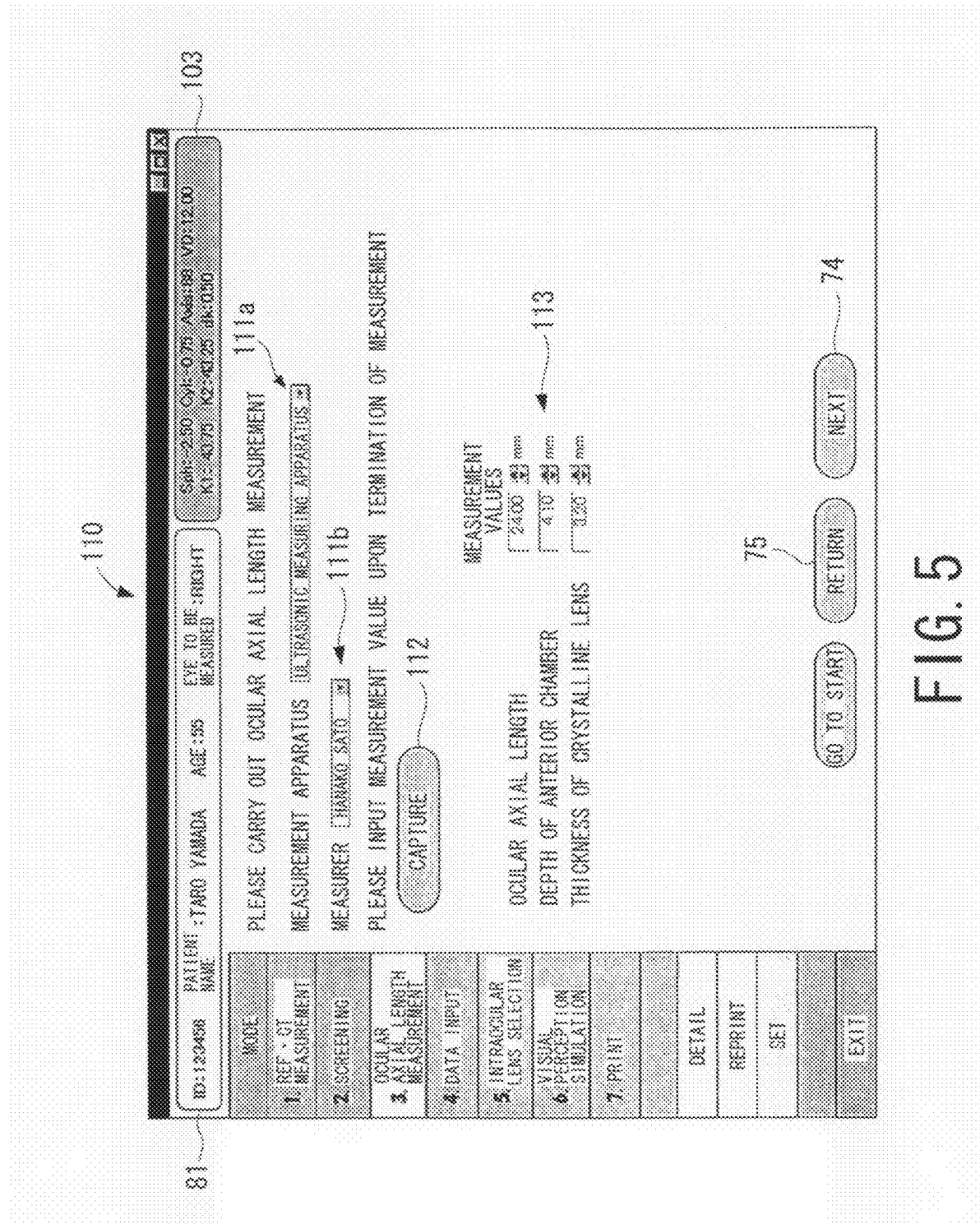
FIG. 5 is a view showing an ocular axial length measurement screen.

After the input is completed in the screen 100 as described above and the button 74 is clicked on, then the CPU 30 enters an ocular axial length measurement screen (or mode) 110 as shown in FIG. 5.

The screen 110 preferably comprises a display field 111a for displaying information pertaining to the apparatus 20, a display field 111b for displaying measurer information, a button 112 for capturing measurement values, and a display field 113 for displaying the captured measurement values. In the preferred embodiment of the present invention, clicking on the button 112 allows the measurement values which are obtained by the apparatus 20 to be stored in the memory 35 and to be displayed on the monitor 50 (in the display field 113). The display field 113 displays each measurement value of the ocular axial length, the depth of the anterior chamber, and a thickness of a crystalline lens. It is added that each measurement value may be changed in predetermined steps.

Further, the CPU 30 determines whether each measurement value of the ocular axial length, the depth of the anterior chamber, and the thickness of the crystalline lens is normal. For example, the ocular axial length is determined to be "normal" when it is equal to or more than 22 mm to less than 28 mm, "abnormality suspected" when equal to or more than 20 mm and less than 22 mm or when equal to or more than 28 mm and less than 30 mm, and "abnormal" when less than 20 mm or when equal to or more than 30 mm. The depth of the anterior chamber is determined to be "normal" when it is equal to or more than 3.5 mm and less than 4.5 mm, "abnormality suspected" when equal to or more than 2 mm and less than 3.5 mm or when equal to or more than 4.5 mm and less than 5 mm, and "abnormal" when less than 2 mm or when equal to or more than 5 mm. The thickness of the crystalline lens is determined to be "normal" when it is equal to or more than 2.5 mm and less than 4 mm, "abnormality suspected" when equal to or more than 2 mm and less than 2.5 mm or when equal to or more than 4 mm and less than 5 mm, and "abnormal" when less than 2 mm or when equal to or more than 5 mm.

Figure 6:
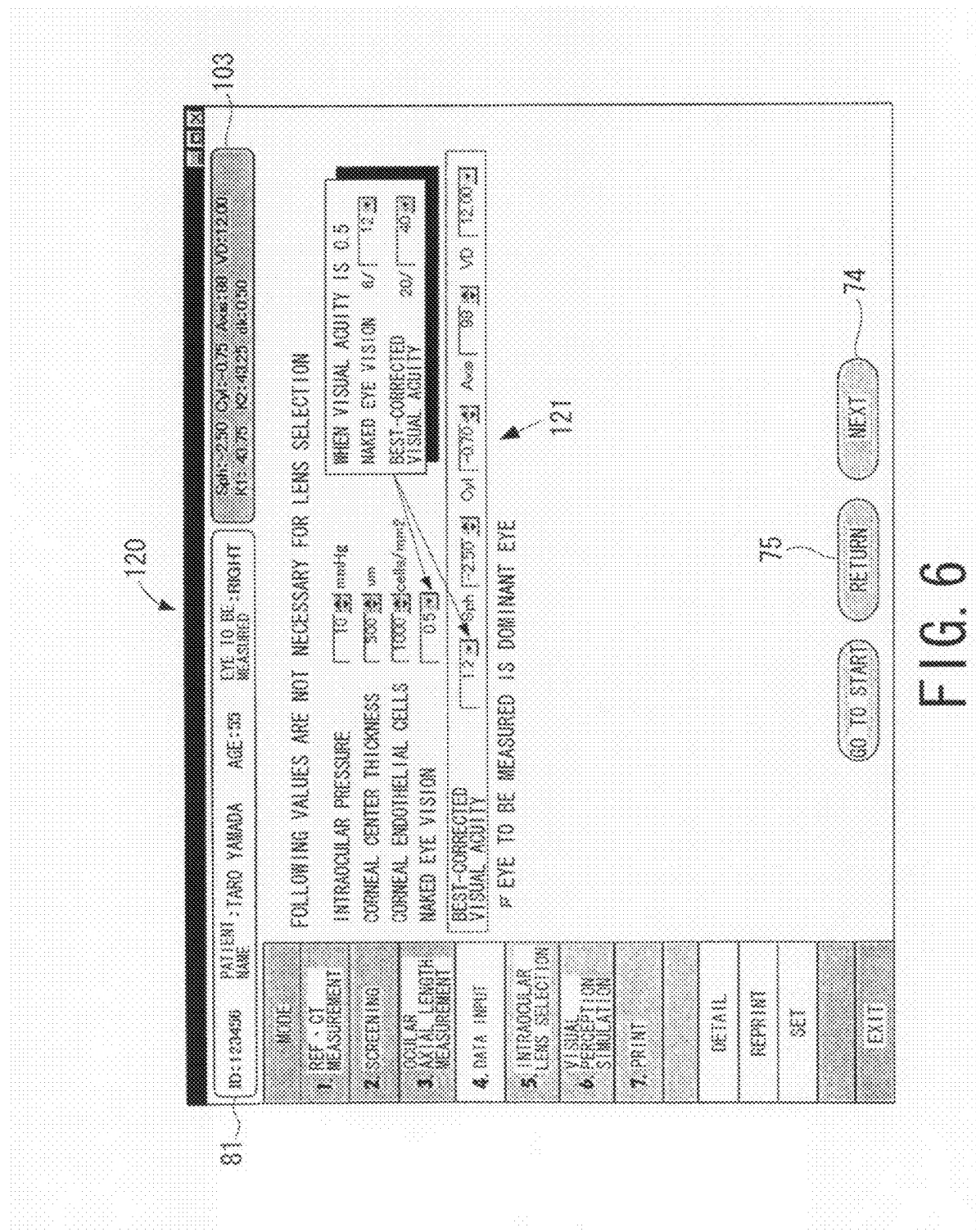
FIG. 6 is a view showing a data input screen.

After the ocular axial length measurement is completed as described above and the button 74 is clicked on, then the CPU 30 enters a data input screen (or mode) 120 as shown in FIG. 6.

The screen 120 preferably comprises a display field 121 for displaying information for use in the prescription of the intraocular lens. In the preferred embodiment of the present invention, the display field 121 preferably displays intraocular pressure, a corneal center thickness, the number of corneal endothelial cells, naked eye vision, best-corrected visual acuity, each of which may be inputted preferably through the input operation. It is added that the CPU 30 determines whether the intraocular pressure, the corneal center thickness, and the number of corneal endothelial cells are normal.

Figure 7:
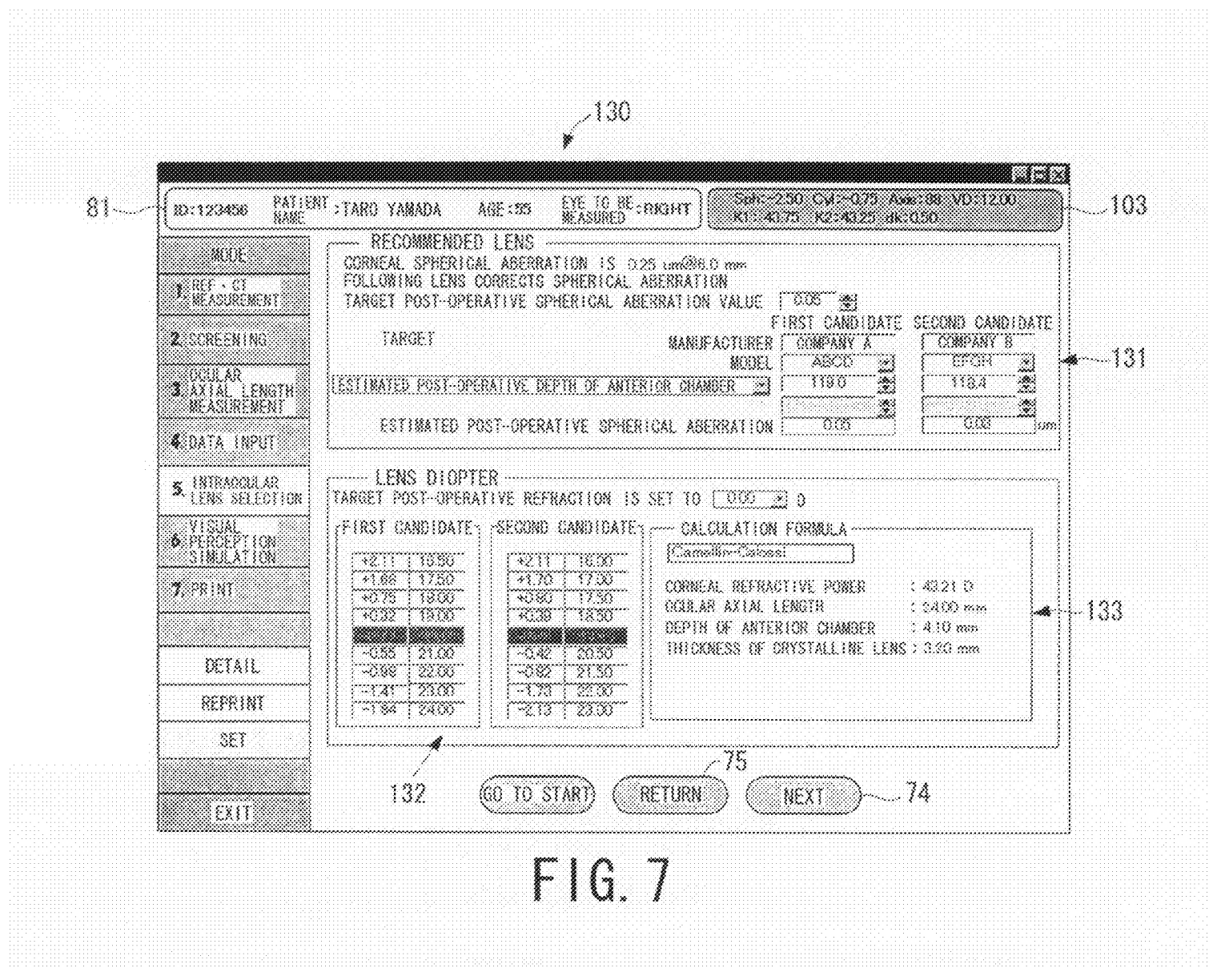

After the data-input operation is completed as described above and the button 74 is clicked on, then the CPU 30 enters an intraocular lens selection screen (or mode) 130 as shown in FIG. 7.

The screen 130 preferably comprises a display field 131 for displaying information pertaining to a recommended intraocular lens model in the plurality of intraocular lens models which have been previously registered in the memory 35, a display field 132 for displaying information pertaining to the diopter of the intraocular lens, and a display field 133 for displaying information pertaining to the calculation formula for finding the diopter of the intraocular lens.

The display field 131 preferably displays a measurement value of the corneal spherical aberration of the examinee's eye, target post-operative spherical aberration (hereinafter, referred to as "target value"), and information pertaining to the specified (or selected) intraocular lens model (the manufacture name, the model name, an estimated post-operative depth of the anterior chamber), estimated post-operative spherical aberration (hereinafter, referred to as "estimated value"). In this case, there are displayed a plurality of candidate intraocular lens models (a first candidate and a second candidate in the preferred embodiment of the present invention) specified (or selected) by the CPU 30.

It is added that the target value may be changed in predetermined steps. According to the preferred embodiment of the present invention, the target value is changed in 0.01 μm steps within the range of −3 μm to +3 μm. Further, the target value is previously stored (or registered) in the memory 35 for each surgeon, and the CPU 30 controls the screen 130 to display the previously stored target value when the CPU 30 enters the screen 130.

The estimated value is indicative of the sum of (or difference between) the corneal spherical aberration of the examinee's eye and the spherical aberration of each intraocular lens model. For example, in FIG. 7 where the corneal spherical aberration of the examinee's eye is +0.24 μm, the estimated values to be obtained when the first and second candidate intraocular lens models are implanted into the examinee's eye become +0.05 μm and +0.03 μm, respectively when the spherical aberrations of the first and second candidate intraocular lens models are −0.19 μm and −0.21 μm, respectively.

The CPU 30 obtains the estimated value of the examinee's eye for each intraocular lens model based on the corneal wavefront aberration of the examinee's eye and the wavefront aberration of each intraocular lens model which have been stored in the memory 35. Then, the CPU 30 compares the set target value and the obtained estimated value with each other for each intraocular lens model, to thereby specify the intraocular lens model which renders the estimated value close to the set target value. Thereafter, the CPU 30 controls the monitor 50 to display information pertaining to the specified intraocular lens model.

According to the preferred embodiment of the present invention, the intraocular lens models are ranked according to a closeness of the estimated value to the target value, and the highly ranked two intraocular lens models are selected as the first and second candidates, respectively. Further, there are displayed the intraocular lens model information and the estimated value for each of the specified intraocular lens models.

Still further, clicking on a predetermined pull-down button allows an at-a-glance display of a pull-down list containing the model names of the intraocular lens models in a high-rank order, whereby a desired model name of the intraocular lens model may be selected from the list, or the currently-selected model name may be changed into a desired model name. Thereafter, when one of the model names is selected from the list for changing, then there are displayed the intraocular lens model information and the estimated value for the selected model name.

The display field 132 preferably displays target post-operative refractive power (Diopter), and a list indicating estimated post-operative refractive power for each of predetermined diopters prepared for the first and second candidate intraocular lens models. It is added that the post-operative refractive power may be changed in predetermined steps. According to the preferred embodiment of the present invention, the target value is changed in 0.5 D steps within the range of −3 D to +3 D.

The CPU 30 calculates the diopter by substitution of the selected target post-operative refractive power, the measurement values of the examinee's eye (the corneal refractive power and the ocular axial length, for example) and the intraocular lens model information into the predetermined calculation formula for finding the diopter of the intraocular lens. Based on the calculated diopter, the CPU 30 specifies the intraocular lens model having the diopter close to the calculated diopter (in the preferred embodiment of the present invention, the plurality of intraocular lens models have been registered in 0.5 D steps, and an intraocular lens having 20 D is specified as the first candidate indicated in FIG. 7, while an intraocular lens having 19.5 D is specified as the second candidate in FIG. 7). Next, there is obtained the estimated post-operative refractive power when the intraocular lens model having the calculated diopter is implanted.

Figure 8:
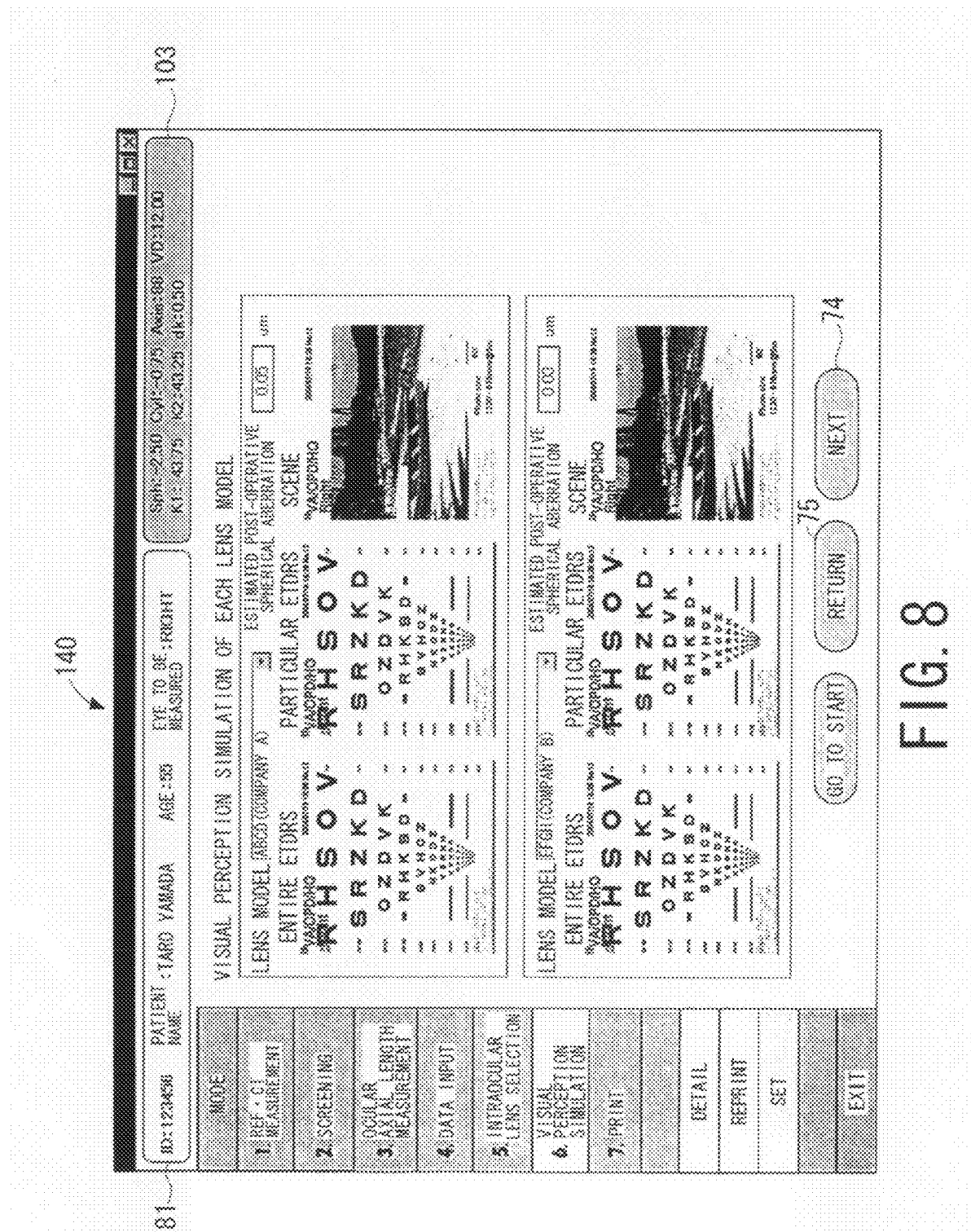
FIG. 8 is a view showing a visual perception simulation screen.

After the intraocular lens model is specified (or selected) as described above and the button 74 is clicked on, then the CPU 30 enters a visual perception simulation screen (or mode) 140 as shown in FIG. 8.

The screen 140 preferably displays the model name of the intraocular lens model, the estimated value, and a predetermined test chart. In the preferred embodiment of the present invention, the screen 140 displays, as the predetermined test chart, an entire chart and a particular chart of an ETDRS (early treatment diabetic retinopathy study) test chart, and a scene.

The CPU 30 displays, in the form of a simulation image, how the examinee visually perceives the predetermined test chart when the specified intraocular lens model is implanted into the examinee's eye, based on the corneal wavefront aberration of the examinee's eye and the wavefront aberration pertaining to each intraocular lens model previously stored in the memory 35. That is to say, the CPU 30 obtains the estimated value based on the corneal wavefront aberration of the examinee's eye and the spherical aberration pertaining to each intraocular lens model, and then the CPU 30 obtains a point spread function based on the obtained estimated value. Thereafter, the CPU 30 performs image processing (i.e., convolution) on the obtained point spread function and the predetermined test chart, to thereby obtain the simulation image of how the predetermined test chart is formed on the surface of a retina of the examinee's eye when the specified intraocular lens model is implanted into the examinee's eye. In the preferred embodiment of the present invention, there are obtained two simulation images corresponding to the specified (or candidate) intraocular lens models, respectively, and the simulation images are displayed on the monitor 50 via the IPU 31.

It is added that the model name of the intraocular lens model may be changed into another model name previously stored in the memory 35. Once the model name is changed, then the CPU 30 obtains the estimated value and the simulation image corresponding to the changed model name, and controls the monitor 50 to display the obtained estimated value and the simulation image, together with the changed model name.

The intraocular lens model may be specified based on any higher-order aberrations other than the spherical aberration. In this case, the sum of the higher order aberration components which is desired to be kept as the post-operative residual higher-order aberration is set as the target value, and correction is performed on the aberration components of the examinee's eye using the aberration components of the intraocular lens, whereby the estimated post-operative residual higher-order aberration is obtained for each intraocular lens model. As a result, the intraocular lens model is specified which renders the estimated value close to the set target value.

Additionally, the intraocular lens model information may include an option for selecting whether or not the intraocular lens is a colored lens. Further, the intraocular lens model information may include an option for selecting a lens material.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An intraocular lens selection apparatus for selecting an intraocular lens (IOL) to be implanted into an examinee's eye, the apparatus comprising:

storing means which stores information on a plurality of IOL models and IOL calculation formulae, the information including a model name, an A constant, and spherical aberration;

first input means which inputs information on any one of a wavefront aberration and an eye refractive power of the examinee's eye, and corneal information including a three-dimensional shape of a cornea of the examinee's eye;

second input means which inputs information necessary to determine an IOL diopter including an ocular axial length of the examinee's eye;

setting means which sets, as target values, a residual wavefront aberration and an eye refractive power of the examinee's eye after the IOL is implanted;

calculation means which (1) obtains a corneal wavefront aberration of the examinee's eye with a corneal aberration assumed to be zero based on the three-dimensional shape of the cornea, and (2) obtains one of the plurality of IOL models and a refractive power which are closest to the set target values based on the obtained corneal wavefront aberration, the information stored in the storing means, and the information input by the first and second input means;

display means; and control means which controls the display means to display a result obtained by the calculation means.

2. The intraocular lens selection apparatus according to claim 1, wherein the control means controls the display means to display a simulation of how a predetermined object is visually perceived by the examinee's eye when the one of the plurality of IOL models is implanted.

* * * * *